United States Patent [19]

Perica et al.

[11] 4,256,117
[45] Mar. 17, 1981

[54] CARDIAC MONITOR WITH STOP WATCH MEANS

[75] Inventors: Jacob E. Perica, 11732 Canterbury, Warren, Mich. 48093; Wayne F. Poyer, Ann Arbor; Neale F. Koenig, Ypsilanti, both of Mich.

[73] Assignee: Jacob E. Perica, Warren, Mich.

[21] Appl. No.: 918,828

[22] Filed: Jun. 26, 1978

Related U.S. Application Data

[62] Division of Ser. No. 662,540, Mar. 1, 1976, Pat. No. 4,096,854.

[51] Int. Cl.³ .............................................. A61B 5/02
[52] U.S. Cl. .................................................. 128/690
[58] Field of Search ....................... 128/670, 687–690, 128/706

[56] References Cited

U.S. PATENT DOCUMENTS

| | | | |
|---|---|---|---|
| 3,803,834 | 4/1974 | Reese | 58/152 R |
| 3,807,388 | 4/1974 | Orr et al. | 128/690 |
| 3,838,684 | 10/1974 | Manuel et al. | 128/690 |
| 3,978,849 | 9/1976 | Geneen | 128/690 |
| 4,053,951 | 10/1977 | Hudspeth et al. | 128/671 |
| 4,086,916 | 5/1978 | Freeman et al. | 128/690 |

*Primary Examiner*—Robert W. Michell
*Assistant Examiner*—Francis J. Jaworski

*Attorney, Agent, or Firm*—Gifford, Van Ophem, Sheridan & Sprinkle

[57] ABSTRACT

A digital stop watch is provided in combination with a cardiac monitor wherein both the stop watch means and the cardiac monitor utilize a common display means and wherein the combination is adapted to be worn around the wrist. The stop watch is of conventional construction, comprising a clock which drives a counter and multiplexing means disposed between the counter and display means for selectively displaying the count in the counter. The cardiac monitor comprises a transducer worn on the body and adapted to produce an electrical pulse in response to each heart beat of the wearer. The transducer output is fed into a rate logic circuit which generates a heart beat rate signal representative of the pulse rate of the wearer and the rate signal is stored in a temporary memory which is continuously and periodically updated. The output from the temporary heart beat memory is fed into the multiplexer so that both the wearer's pulse rate and the elapsed time of the stop watch may be alternatively displayed on the common display means by manually activating the multiplexer. In the preferred form of the invention, a pair of separated pulse rate values are preset by the user and are then stored in the cardiac monitor so that an indicator is activated when the pulse rate exceeds one of the rate values or drops below the other rate value.

3 Claims, 3 Drawing Figures

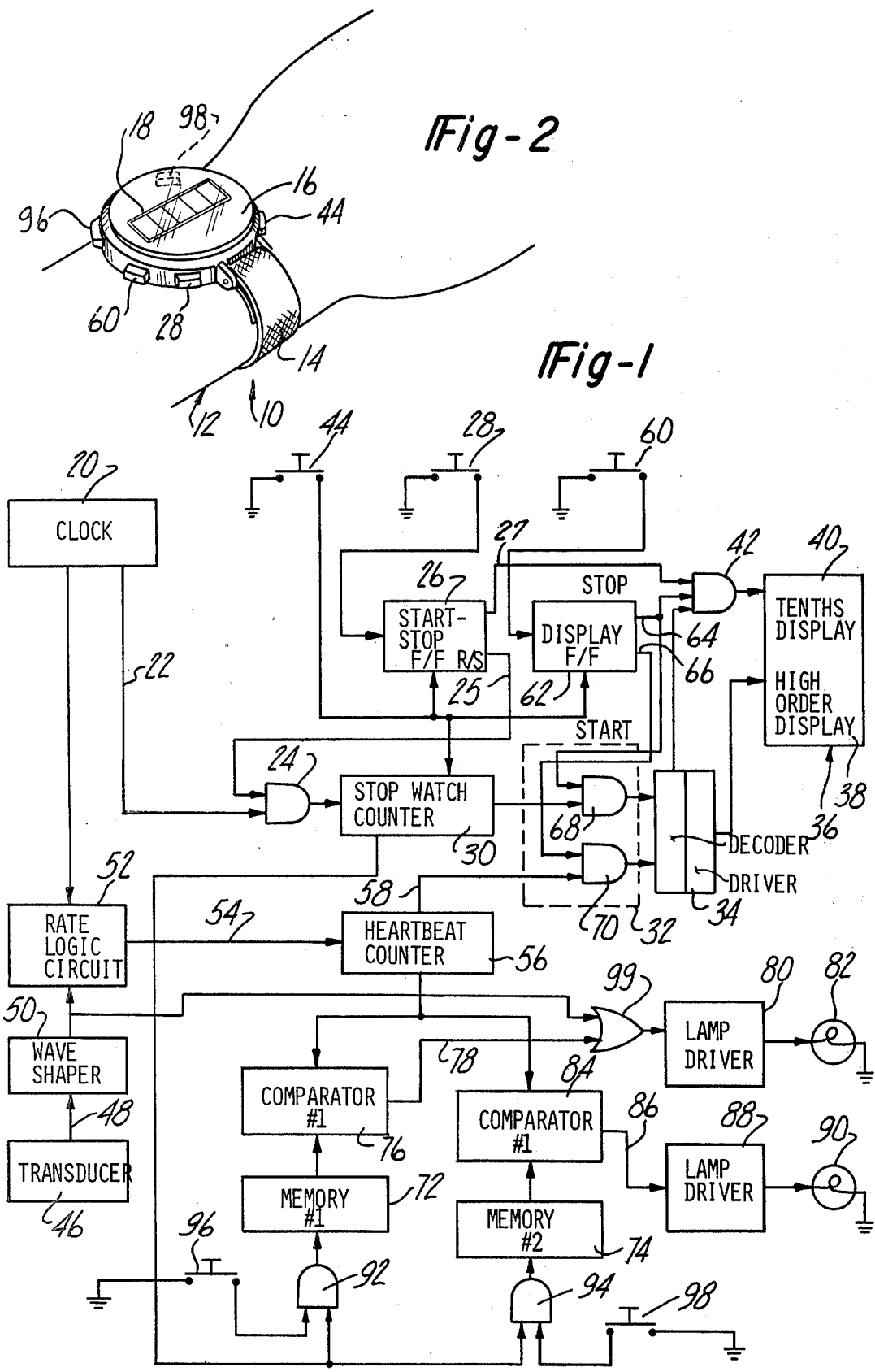

CARDIAC MONITOR WITH STOP WATCH MEANS

CROSS REFERENCE TO RELATED APPLICATIONS

This is a division of application Ser. No. 662,540 filed Mar. 1, 1976, now U.S. Pat. No. 4,096,854.

BACKGROUND OF THE INVENTION

I. Field of the Invention

The present invention relates generally to a combination stop watch and heart beat monitor and more particularly, to a heart beat monitor in which indicating means are activated when preset limits of minimum and maximum pulse rate limits are exceeded.

II. Description of the Prior Art

There has been no previous pulse rate monitor with the specific capability of enabling the user to engage in physical activity at a pre-determined pulse rate and for whatever time might be desired.

There are cardiac monitors which generate an output signal representative of the pulse rate of the wearer. Such monitors have been previously used on cardiac patients during their illness, recovery and/or recuperation. Recently, some monitoring of heart beat function has been done in connection with stress testing, such as the tread mill tests.

These previously known pulse monitors, however, have been directed to a different function than this device. Furthermore, they have lacked the flexibility and portability which this device can offer. For example, a person going out to jog for an hour could in no way transport an electro-cardiograph or other existing devices to let him known on a continuous basis what his pulse rate was at any given time during his workout. Without the device, the person so exercising must stop his activity and manually take his pulse. The disadvantage of this is clear because as soon as the activity stops, the pulse rate begins to decrease. Thus, an accurate measure of the pulse rate during athletic activity is impossible.

Certain laboratory equipment does exist which can accurately measure heart rate during exercise but this equipment lacks the portability to be of any value to the average athlete. Furthermore, the cost is prohibitive.

In the newly emerging field of pulsometrics, the information provided by this device is essential. The primary function of the device is to assist athletes and others interested in increasing their physical capabilities.

There are certain recognized techniques of exercise physiology which relate to our device. First, there is the overload principle. This relates to strengthening the heart muscle by causing it to do more work than normal. During exercise, there is an increased return of blood from the veins, which gives the heart resistance to beat against. It is this resistance or loading which causes the heart to develop. Secondly, there is progression which merely states that if physical condition is to improve, a person must be repeatedly exposed to new, higher levels of overload.

It is well to remember that each person reponds to a training program in his own way and at his own rate. Therefore, no specific recomendations are made. An individual seeking to improve his physical condition through use of this device would be well advised to consult with a physician skilled in the art such as preventative cardiology.

Reference should also be had to "The Official YMCA Physical Fitness Handbook", Pages 67-84, published in 1975, and "Total Fitness In 30 Minutes A Week" by Moorehouse & Gross, published in 1975, both of which describe the physical fitness overload theory in greater detail.

SUMMARY OF THE PRESENT INVENTION

The present invention obviates the above mentioned disadvantages of the previously known cardiac monitors by providing a cardiac monitor adapted to be worn around the wrist in combination with a stop watch so that either the heart beat pulse rate or the elapsed time on the stop watch may be displayed on common display means provided on the monitor. In addition, the heart beat pulse rate is continuously compared to a pair of preset separated pulse rate limits so that when the heart beat rate exceeds the maximum heart beat rate or drops below the minimum heart beat rate, an appropriate indicator is activated.

The stop watch portion of the present invention comprises an oscillator having its output selectively fed to a counter so that the count in the counter is representative of the elapsed time on the stop watch. The counter output is fed to a dual input multiplexer while the output of the multiplexer is conected to a digital display means such as a LED display. Thus the multiplexer may selectively display the elapsed time, as represented by the count in the counter, on the display means.

The cardiac monitor comprises a transducer secured to the wearer and adapted to generate an electrical pulse in response to each heart beat. The output from the transducer is fed to a rate logic circuit which generates an output signal representative of the heart beat pulse rate. The rate logic circuit output is stored in a second counter having its output connected to the second input of the multiplexer so that the heart beat pulse rate may be displayed via the multiplexer on the display means.

In addition, the heart beat rate is continuously contrasted with a pair of separated preset heart beat rate limits so that when the upper heart beat rate limit is exceeded, a high pulse rate indicator is activated.

It can thus be seen that the present invention provides a novel combination for both monitoring the heart beat pulse rate and providing a stop watch wherein both the pulse rate and the stop watch elapsed time may be displayed on a common display means. Moreover, the heart beat pulse rate is continuously compared with a pair of separated preset limits and appropriate indicators are activated when the heart beat rate falls below the lower preset limit or exceeds the upper preset limit thereby eliminating the necessity of periodically checking the cardiac monitor. Furthermore, as will become shortly apparent, the combination stop watch and cardiac monitor of the present invention is adapted to be worn about the wrist and totally contained within a single relatively small package which is now possible due to microelectronics.

BRIEF DESCRIPTION OF THE DRAWING

A better understanding of the present invention will be had upon reference to the following detailed description when read in conjunction with the accompanying drawing wherein like reference characters refer to like parts throughout the several views, and in which:

FIG. 1 is a block circuit diagram showing the combination stop watch and cardiac monitor of the present invention, FIG. 2 is a perspective view showing the combination stop watch and cardiac monitor mounted around the wrist of a wearer.

DETAILED DESCRIPTION OF THE PRESENT INVENTION

Figure 3:
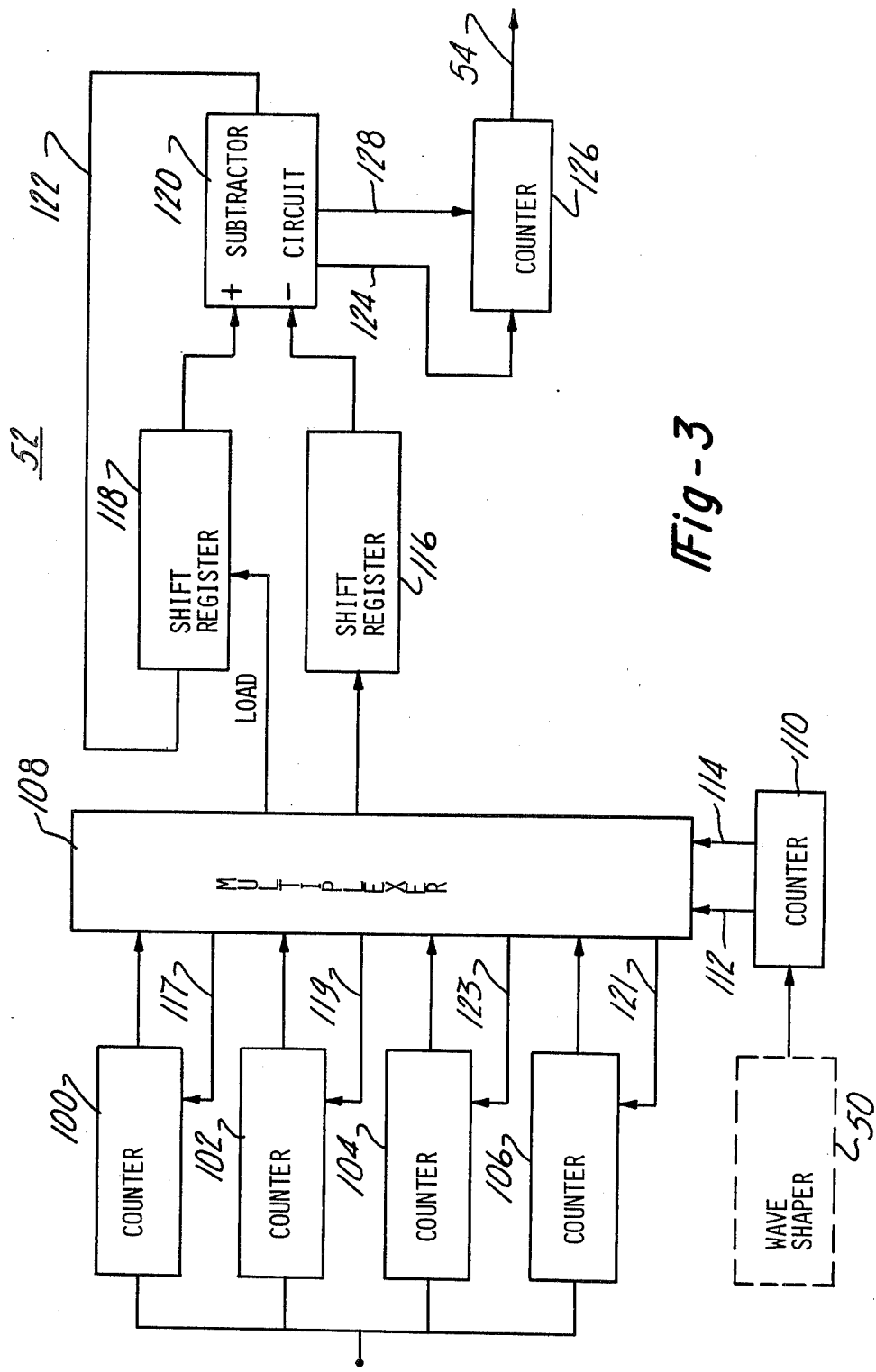
FIG. 3 is a block circuit diagram showing an exemplary rate logic circuit for the cardiac monitor of the present invention.

Referring first to FIG. 2, the combination stop watch and cardiac monitor 10 is there shown mounted about the wrist 12 of a wearer by a strap 14. The device 10 includes a housing 16 which encases and supports the electronic components to be hereinafter described, and also includes a display means 18 such as a five digit LED or liquid crystal digital display.

The circuit diagram for the combination stop watch and cardiac monitor 10 is illustrated in FIG. 1. For purposes of description only, the stop watch function will be described first and separately from the cardiac monitor.

As shown in FIG. 1 a clock 20 such as a mechanical tuning fork oscillator or an electronic oscillator provides a basic timing output for the stop watch and in particular preferably produces a 10 CPS pulse along a line 22 to an AND gate 24. The second input to the ANd gate 24 is coupled to one output 25 from a start-stop flip flop 26. A switch 28 is provided externally of the housing 16 on the device 10 so that actuation of the switch 28 sets the flip flop 26 and output 25 to a high condition so that the clock signal on line 22 is gated through the AND gate 24 and into the input of a counter 30. The switch 28 is preferably a pushbutton switch and a subsequent depression of the pushbutton switch 28 will set the output 25 of the flip flop 26 to a low condition thereby disabling the AND gate 24. In this manner, assuming the count in the counter 30 was initially zero, it can be seen that the count in the counter 30 is representative of the elapsed time between the depressions of the pushbutton switch 28.

The output from the counter 30 is fed through a multiplexer 32, in a manner to be later described, to a decoder/driver 34, such as a seven segment display decoder. The output from the decoder/driver 34 in turn is fed to a display means 36, such as a five digit LED or liquid crystal display. As illustrated, the display means 36 is further divided into a higher order display 38 which is directly connected to the decoder/driver 34, and a lower order display 40 which is coupled via a three input AND gate 42 to the decoder/driver 34. One input of the AND gate 42 is coupled to the other output of the start/stop 26 so that the lower order display 40 is illuminated only when the second output 27 of the flip flop 26 is in a high condition, or in other words, when the AND gate 24 is disabled. This particular construction has proven desirable since the lower order displays 40 preferably display the elapsed time in tenths of a second. Consequently, the display would be unreadable while the stop watch is "running" and the AND gate 42 therefore turns off the lower order display 40 when the stop watch is running to conserve power and elongate the life of the battery.

The stop watch, of course, includes a reset pushbutton switch 44 which upon actuation sets the start/stop flip flop to its stop condition and simultaneously resets the stop watch counter 30.

The cardiac monitor generally comprises a transducer 46 which is preferably positioned at the base of the housing 16 adjacent the wrist 12 of the wearer. By fastening the straps 14 of the device 10 securely around the wrist 12, the transducer 46, which may be a conventional pressure transducer, will detect each heart beat pulse and generate an electrical pulse along its output line 48 in response thereto. The output line 48 in turn is coupled through a wave shaper 50 to a rate logic circuit 52. The rate logic circuit 52 also receives input signals from the clock 20 and generates an output along the line 54 which is representative of the pulse rate of the wearer. The rate logic circuit 52 will be later described in greater detail.

The output 54 of the rate logic circuit 52 is fed into the input of a heart beat counter 56 so that the count in the counter 56 is representative of the heart beat rate of the wearer. It is to be understood, of course, that the count in the counter 56 must be periodically and continuously refreshed and updated and this may be accomplished by any conventional construction. The output 58 from the heart beat counter 56 is fed into the second input of the multiplexer 32 so that the pulse rate from the counter 56 may be selectively displayed on the display means 36.

A display pushbutton switch 60, a display flip flop 62 and the multiplexer 32 are provided so that the wearer may selectively display either the elapsed time from the stop watch counter 30 or the pulse rate from the heart beat counter 56. The display flip flop 62 includes first and second outputs 64 and 66, respectively, and activation of the switch 60 changes the state of both outputs 64 and 66 in the conventional fashion. When the output 64 of the display flip flop 62 is in a high condition, the output 66 is in a low condition, the count from the stop watch counter 30 is gated through an AND gate 68 to the decoder/driver 34 so that the stop watch elapsed time is displayed on the display means 36. Conversely, depression of the display pushbutton 60 switches the output 66 to a high condition and the output 64 to a low condition. Thus the AND gate 68 is disabled and instead an AND gate 70 is enabled so that the count in the heart beat counter 56 is gated through the AND gate 70 to the driver/decoder 34 for display on the display means 36. It will be understood, however, that the AND gates 68 and 70 are illustrated in simplistic form and that in practice, a number of AND gates 68 and 70 would be required for each display digit and likewise a separate decoder/driver 34 would conventionally be required for each display digit.

The cardiac monitor further includes a first memory 72 and a second memory 74 in which a pair of separated preset limits are stored in a manner to be shortly described. A lower limit for the heart beat rate is stored in the first memory 72 and is compared with the count in the heart beat counter 56 by a comparator 76. Whenever the count in the first memory 72 equals or exceeds the count in the heart beat counter 56, the comparator 76 generates an output signal along line 78 to driver 80 which drives an indicator 82 such as a lamp. In this manner, whenever the heart beat rate of the wearer falls below the preset limit stored in the first memory 72, the indicator 82 is activated. A second comparator 84 is also provided to compare the count in the second memory 74 with the count in the heart beat counter 56. However, in contrast to the first comparator 76, the second comparator 84 generates an output signal along line 86 whenever the count in the heart beat counter 56 equals or exceeds the count in the second memory 74. The output line 86 is connected to a driver 88 which in turn drives an indicator 90 such as a lamp. Thus whenever the pulse rate of the wearer exceeds the preset limit stored in the second memory 74, the indicator 90 is activated.

Preferably the output from the wave shaper 50 is combined with the line 78 by an OR gate 99 so that the indicator lamp 82 blinks with each heart beat. This connection is desirable in that it provides a visual indication that the transducer 46 is properly detecting the wearer's heart beat.

In the preferred form of the invention, the wearer may establish the preset heart beat rate limits stored in the first and second memories 72 and 74 in the following manner. The output of AND gates 92 and 94 are respectively fed to the load inputs of the first and second memories 72 and 74. An output from the stop watch counter 30 is fed to one input of each of the AND gates 92 and 94 while pushbutton switches 96 and 98 are respectively connected to the second inputs of the AND gates 92 and 94. Consequently, activation of the pushbutton switch 96 gates the counter output 30 into the first memory 72 through the AND gate 92 while conversely depression of the second pushbutton switch 98 gates the counter output 30 through the AND gates 94 into the second memory 74. Thus the wearer may easily set the pulse rate limits by merely depressing switch 96 or 98 with the stop watch running and releasing switch 96 or 98 when the elapsed time in second equals the desired pulse rate limit.

An exemplary rate logic circuit 52 is illustrated in FIG. 3 and for the purposes of illustration it will be assumed that the rate logic circuit 52 generates a heart beat rate signal along the line 54 which is the heart pulse rate averaged over four heart beats. However, the heart beat rate signal will be updated for each heart beat.

The rate logic circuit 52 includes four counters 100, 102, 104, and 106 which have their outputs fed into a multiplexer 108. A clock frequency f, for example 100 Hz, from the clock 20 is fed to the inputs of the counters 100–106 so that each of the counters 100–106 continuously counts at the frequency f.

The output from the wave shaper 50 is fed into the input of a two bit binary counter 110 which has its outputs 112 and 114 coupled to the control inputs of the multiplexer 108. The binary counter 110 counts from binary zero to binary three and for each different count from the counter 110, the multiplexer 108 transfers the contents of a different one of the counters 100–106 into a shift register 116. Thus, for example, when the counter 110 counts to a binary two, the contents of the counter 104 are transferred into the shift register 116. Likewise, when the counter 110 counts to a binary three, the contents of the counter 106 are transferred into the shift register 116 by the multiplexer 108 and so on for the counters 100 and 102. Immediately after the contents of any of the counters 100–106 are transferred into the shift register 116, the multiplexer 108 resets that counter to zero by a reset signal along the respective reset lines 117, 119, 121, 123.

The contents of the shift register 116 thus equals the frequency rate f multiplied by the time elapsed during the previous four heart beats. Thus if the contents of the shift register 116 are divided into a number equal to $60 \times f \times N$ where N equals the number of counters 100–106, the quotient of this division will equal the heart beat pulse rate. In the example shown, f equals 100 and N equals 4 so that the divisor for the example shown would be the number 24,000.

Any conventional divider may be utilized to divide the contents of the shift register 116 into the divisor which in this case is 24,000. However, as shown in FIG. 3, when the contents of any one of the counters 100–106 are loaded into the shift register 116, the multiplexer 108 simultaneously loads the number 24,000 into a second shift register 118. The contents of both registers 118 and 116 are then successively fed serially through a serial subtractor circuit 120 which subtracts the number in the shift register 116 from the number in the shift register 118 in the conventional manner. The result of this subtraction is fed along an output line 122 from the subtractor 120 and reloaded back into the shift register 118 and the subtraction operation is again repeated. The subtractor circuit 120 generates an output pulse along a line 124 for each completed subtraction to the input of a binary counter 126. When the subtraction of the contents of shift register 116 from the shift register 118 results in a negative number, the subtractor circuit 120 generates a signal along a line 128 which disables the counter 126. In this manner, when the counter 126 is disabled by the signal line 128, the count in the counter 126 represents the quotient of the division of the contents of the shift register 116 into the shift register 118. The count in the counter 126 thus represents the heart beat pulse rate and this signal is fed along line 54 to the heart beat counter 56 as previously discussed.

The rate logic circuit 52 thus averages the heart beat pulse rate over four heart beats and updates the heart beat rate signal on line 54 for each heart beat. It should be apparent, however, that by merely changing the number of counters 100–106 and the initial contents of the shift register 118, the heart beat rate may be averaged over any desired period and still continuously updated with each heart beat.

It can thus be seen that the combination stop watch and cardiac monitor of the present invention provides a novel combination unknown in the prior art. In particular, the display pushbutton 60 permits the wearer to selectively display either the elapsed time on the stop watch counter or the heart beat rate of the wearer on the common display means 36. In addition, the warning indicators 82 and 90 are activated whenever the heart beat rate falls outside of a predetermined rate limits as contained in the memories 72 and 74. Moreover the rate limits in the memories 72 and 74 are preset by the wearer and may be reset to different values by the user at any desired time.

Having described our invention, many modifications thereto will become apparent to those skilled in the art to which it pertains without deviation from the spirit of the invention as defined by the scope of the appended claims.

What is claimed is:
1. In combination:
   a digital stop watch, said stop watch comprising a stop watch counter, a clock and switch means for selectively feeding said clock output into the input of said stop watch counter so that the count in the stop watch counter is representative of the elapsed time from the actuation of said switch means, display means and means for selectively displaying the count in said counter on said display means, and
   a body worn cardiac monitor comprising:

transducer means secured to the body of the wearer and adapted to detect heart beats and to produce an electrical signal representative thereof, means for receiving the signals from said transducer means and producing a heart beat rate signal representative of the heart beat rate per unit time, and multiplex means for selectively displaying either the count in said stop watch counter or the heart beat rate on said display means.

2. The combination as defined in claim 1, and including means for establishing a pair of separated pulse rate limits, means for comparing said heart beat rate signal with said rate limits and means for actuating indicators means whenever the heart beat rate exceeds one of said preset limits or falls below the other preset limit.

3. The combination as defined in claim 2, wherein the means for establishing said rate limits further comprises a pair of memories and means for selectively feeding the count from said stop watch counter into either of said memories.

* * * * *